United States Patent
Brandhoff

(10) Patent No.: US 6,544,204 B1
(45) Date of Patent: Apr. 8, 2003

(54) SYNTHETIC RIGID BANDAGE

(75) Inventor: Stefan Brandhoff, Andernach (DE)

(73) Assignee: Lohmann GmbH & Co. KG (DE)

( * ) Notice: Subject to any disclaimer, the term of this patent is extended or adjusted under 35 U.S.C. 154(b) by 0 days.

(21) Appl. No.: 09/647,562

(22) PCT Filed: Mar. 26, 1999

(86) PCT No.: PCT/EP99/02077

§ 371 (c)(1),
(2), (4) Date: Dec. 1, 2000

(87) PCT Pub. No.: WO99/51281

PCT Pub. Date: Oct. 14, 1999

(30) Foreign Application Priority Data

Apr. 2, 1998 (DE) .......................... 198 14 826
Sep. 11, 1998 (DE) .......................... 198 41 561

(51) Int. Cl.⁷ ................................. A61F 5/00
(52) U.S. Cl. .................. 602/8; 602/1; 602/5; 602/6
(58) Field of Search ............. 602/1, 16, 20, 602/23–26, 29, 3, 6, 8

(56) References Cited

U.S. PATENT DOCUMENTS

| 3,645,835 A | * 2/1972 | Hodgson | 428/195 |
| 3,656,475 A | 4/1972 | Hanrahan, Jr. | 128/90 |
| 4,326,509 A | 4/1982 | Usukura | 128/90 |
| 4,899,738 A | 2/1990 | Parker | |
| 4,968,542 A | 11/1990 | Gasper et al. | 428/76 |
| 5,027,803 A | 7/1991 | Scholz et al. | |
| 5,603,691 A | 2/1997 | Scholz et al. | |

FOREIGN PATENT DOCUMENTS

| DE | 23 57 931 | 5/1975 | ............ B32B/5/28 |
| EP | 0393003 | 5/1993 | |
| WO | WO94/27648 | * 12/1994 | |
| WO | 95/19751 | 7/1995 | |

* cited by examiner

Primary Examiner—Michael A. Brown
Assistant Examiner—Lalita M Hamilton
(74) Attorney, Agent, or Firm—D. Peter Hochberg; Katherine R. Vieyra; Sean Mellino

(57) ABSTRACT

A synthetic rigid bandage especially for splinting and/or supporting a diseased or injured limb of the human or animal apparatus of locomotion, comprising a curable core which is formed by one or more synthetic resin-impregnated layers of longitudinal strips of a textile fabric, is covered at the one side thereof with a pad and on the other side thereof with a water vapour-pervious, longitudinally and/or transversally elastic film or sheet cover, and is to be stored in a moisture-proof package, said core being mouldable in its ready-for-application state, is characterized in that the said film or sheet cover is separated from the said resin-impregnated layers by means of a spacer.

7 Claims, 1 Drawing Sheet

SYNTHETIC RIGID BANDAGE

BACKGROUND OF THE INVENTION

This invention relates to a synthetic rigid bandage especially for splinting and/or supporting a diseased or injured limb, comprising a curable core which is formed by one or more synthetic resin-impregnated layers of longitudinal strips of a textile fabric, is covered at the one side thereof with a pad and on the other side thereof with a water vapour-pervious, longitudinally and/or transversally elastic film or sheet cover, and is to be stored in a moisture-proof package, said core being mouldable in its ready-for-application state.

DESCRIPTION OF THE PRIOR ART

The state of the art includes a large number of documents describing orthopaedic splints or supports, whose materials as well as the means for manufacturing are in principle largely similar to those described in the introductory part of claim 1 of the subject matter of the application. Textile substrates of natural or synthetic and frequently glass fibres are mostly used as starting materials; these are impregnated with a curable synthetic resin and are stored—mostly in the form of a roll—in a film envelope, protected against access of a curing medium. As curing agents are provided, inter alia:

a) Ultraviolet or X-rays; e.g. in interaction with polyurethane and a photoinitiator according to U.S. Pat. No. 3,656,475.

b) Action of heat; for instance, an orthopaedic bandage of thick textile material with a thermoplastic composition containing 60–80%-wt. of saturated linear polyester and 20–40%-wt. of resin with a low crystallization point and a softening temperature of about 45° C. is cured according to U.S. Pat. No. 4,326,509.

c) Air humidity or water; for instance, a textile substrate is impregnated with resin from the group of water-curable isocyanates, stored in a porous envelope and is impregnated in water for curing, according to DE-PS 23 57 931.

d) Semirigid, resilient supports for injured or diseased limbs are known from U.S. Pat. No. 4,968,542 and are likewise cured by a reaction between resin and curing agent.

From multiple negative experience it has turned out as a disadvantage in the stocking of resin-impregnated textile substrates that in common systems of the above-described kind which comprise resin-impregnated cores after an unpredictable time of storage the resin penetrates or bleeds through the cover. This leads to skin contact with the hands of the user and thereby to a possible risk since the user is to work without a corresponding protective device (gloves). Moreover, the product is rendered unusable.

SUMMARY OF THE INVENTION

The object of this invention is to improve a synthetic rigid bandage of the kind mentioned in the introductory part of claim 1 in such a way that in the stocking of resin-impregnated textile fabrics or nonwovens even for an extended period of time the passage of resin through the cover is securely prevented, using uncomplicated and inexpensive means.

DESCRIPTION OF THE PREFERRED EMBODIMENT

Figure 1:
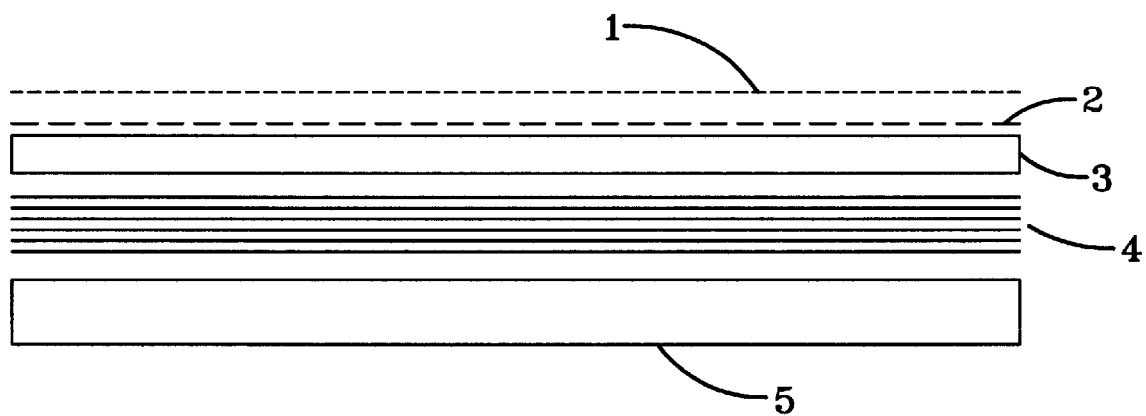
FIG. 1 is a schematic sketch of a rigid bandage of the invention.

To achieve this object in a synthetic rigid bandage of the kind mentioned at the outset, it is proposed according to the invention that a spacer 3 is introduced between the film or sheet cover 1 and the resin-impregnated core 4 which is connected with the film as the outer layer by a segmental, water vapor-permeable pressure-sensitive adhesive coating. FIG. 1 shows a preferred embodiment of the invention having a water vapor-pervious, longitudinally and/or transversally elastic film or sheet cover 1, a water vapor-permeable pressure-sensitive adhesive coating 2, a spacer 3 made up of a hydrophobic, air-permeable, longitudinally and/or transversally nonwoven elastic, a curable core 4 of synthetic resin-impregnated layers of longitudinal strips of a textile fabric, and a pad 5.

By applying, for example, a hydrophobic, air-permeable and longitudinally and/or transversally elastic nonwoven, a cotton wool, a plastic foam or a textile fabric onto the inner wall of the cover film, a disadvantageous contact between resin and film is prevented so that bleeding-through of the resin and its disadvantageous consequences are prevented completely.

The spacer does not suck the resin out from the layers of the core and the segmental pressure-sensitive adhesive coat between spacer and film leads to an optimal comprehensive solution which on the one hand does not diminish the water vapour-pervious property of the film and on the other can be performed at negligibly low cost. Also, the laminate formed in this manner remains longitudinally and transversally elastic so that the rigid bandage can be applied to a part of the body, e.g. an arm or a leg, free from folds or creases and moreover dries within an appropriate time.

Further embodiments of the invention are provided according to the subclaims.

One embodiment of the rigid bandage provides that the layers of longitudinal strips forming the core are impregnated with polyurethane resin.

This resin is especially suitable for curing by means of air humidity or water.

One may make use of the measure that the nonwoven consists 100% of polyester fibres.

Furthermore the invention provides that the layer of nonwoven forms a laminate with the cover film, said laminate being longitudinally and transversally elastic and being water vapour-permeable.

Finally, one embodiment provides that the layer of the hydrophobic synthetic cotton wool has a thickness between 1 and 8 mm, preferably between 1.5 and 5 mm, and especially preferred 2.5 mm.

The use of the synthetic rigid bandage according to the invention is uncomplicated and time-saving since the padding of a simple rigid bandage can be dispensed with. Handling is easy, gloves are not required, the so-called plaster room remains clean.

The width and length of the rigid bandage is chosen in accordance with the indication, and the required length is removed from the package.

The site of the cut is immediately closed carefully in order to avoid curing caused by access of air humidity. For this purpose, the material end is preferably folded inwardly over several centimetres and closed moisture-tight. Then, the severed rigid bandage is dipped into water tempered to about 20–30° C., is subsequently folded and excess water is pressed out. Then, by slightly stretching, the pad is drawn over the glass fibre cutting edges. For application, the mouldable material is fixed with an elastic bandage at an end thereof, subsequently it is moulded by hand to the body part to be supported, and then one has to wait, if possible without movement, until the rigid bandage has set in 3 to 5 minutes.

The invention is uncomplicated and inexpensive and prevents the unwanted contact between resin and film, so that the bleeding-through of the resin is prevented along with its disadvantages. In this respect the invention constitutes an optimum solution of the task posed at the outset.

The invention has been described in detail with particular reference to the preferred embodiment, but variations and modifications within the spirit and scope of the invention may occur to those skilled in the art to which the invention pertains.

What is claimed is:

1. A synthetic rigid bandage especially for splinting and/or supporting a diseased or injured limb of a human or animal comprising a curable core which is formed by at least one synthetic resin-impregnated layer of longitudinal strips of a textile fabric, said core being covered at the one side thereof with a pad and on the other side thereof with a water vapor-pervious, longitudinally and/or transversely elastic film or sheet cover, the bandage being stored in a moisture-proof package, said core being moldable in its ready-for-application state, wherein said film or sheet cover is separated from the said resin-impregnated layers by means of a spacer made up of a hydrophobic, air-permeable, longitudinally and/or transversely elastic nonwoven material.

2. The rigid bandage according to claim 1, wherein the textile fabric forming the core is impregnated with polyurethane resin.

3. The rigid bandage according to claim 1, wherein the spacer is connected with the covering film or sheet by means of a water vapor-permeable pressure-sensitive adhesive coating.

4. The rigid bandage according to claim 3, wherein the pressure-sensitive adhesive coating is segmental.

5. The rigid bandage according to claim 1, wherein the spacer of the film or sheet cover is selected from the group consisting of a water-repellant textile fabric, nonwoven plastic and foamed plastic.

6. The rigid bandage according to claim 1, wherein the spacer forms a laminate with the outer plastics film, said laminate being longitudinally and transversely elastic.

7. The rigid bandage according to claim 1, wherein the spacer has a thickness of between 1 and 8 mm.

* * * * *